United States Patent
Biedermann et al.

(10) Patent No.: US 9,861,388 B2
(45) Date of Patent: Jan. 9, 2018

(54) RECEIVING PART FOR COUPLING A BONE ANCHOR TO A ROD AND BONE ANCHORING DEVICE WITH SUCH A RECEIVING PART

(71) Applicant: BIEDERMANN TECHNOLOGIES GMBH & CO. KG, Donaueschingen (DE)

(72) Inventors: Lutz Biedermann, VS-Villingen (DE); Bernd Fischer, Bräunlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/946,583

(22) Filed: Nov. 19, 2015

(65) Prior Publication Data

US 2016/0143665 A1    May 26, 2016

Related U.S. Application Data

(60) Provisional application No. 62/082,517, filed on Nov. 20, 2014.

(30) Foreign Application Priority Data

Nov. 20, 2014   (EP) .................................... 14194064

(51) Int. Cl.
   *A61B 17/70*    (2006.01)
   *A61B 17/86*    (2006.01)

(52) U.S. Cl.
   CPC ...... *A61B 17/7002* (2013.01); *A61B 17/7032* (2013.01); *A61B 17/7037* (2013.01); *A61B 17/8605* (2013.01)

(58) Field of Classification Search
   CPC .................................................. A61B 17/7002
   See application file for complete search history.

(56) References Cited

U.S. PATENT DOCUMENTS

| 7,731,736 B2 | 6/2010 | Guenther et al. |
| 8,465,528 B2 * | 6/2013 | Schumacher ...... A61B 17/7032 606/270 |

(Continued)

FOREIGN PATENT DOCUMENTS

FR    2 904 526 A1    2/2008

OTHER PUBLICATIONS

Extended European Search Report issued by the EPO for EP 14194064.3 dated May 8, 2015 (7 pages).

*Primary Examiner* — Ellen C Hammond
*Assistant Examiner* — Stuart S Bray
(74) *Attorney, Agent, or Firm* — Lewis Roca Rothgerber Christie LLP

(57) ABSTRACT

A receiving part for coupling a bone anchor to a rod is provided, where the bone anchor includes a shank for anchoring to a bone or a vertebra. The receiving part includes a first end and a second end, the second end being connected to the shank, a bore extending from the first end into the receiving part for receiving a fixation device, the bore having a bore axis, and a recess for receiving a rod, the recess being open at the first end of the receiving part for allowing insertion of the rod and having opposing sidewalls on at least one side of the bore. When a rod is inserted into the recess, a longitudinal axis of the rod extends substantially perpendicular to the bore axis. A resilient retention element is provided on at least one of the opposing sidewalls, where the resilient retention element is deflectable toward the at least one sidewall when the rod is inserted.

22 Claims, 10 Drawing Sheets

(56) References Cited

U.S. PATENT DOCUMENTS

| | | | | |
|---|---|---|---|---|
| 8,506,609 | B2* | 8/2013 | Biedermann | A61B 17/7037 606/266 |
| 8,512,382 | B2* | 8/2013 | Cawley | A61B 17/7035 606/265 |
| 8,663,298 | B2* | 3/2014 | Keyer | A61B 17/7037 606/304 |
| 9,034,022 | B2* | 5/2015 | Asaad | A61B 17/8605 606/308 |
| 9,254,150 | B2* | 2/2016 | Biedermann | A61B 17/7037 |
| 9,282,998 | B2* | 3/2016 | Schlaepfer | A61B 17/7032 |
| 9,320,546 | B2* | 4/2016 | Keyer | A61B 17/7007 |
| 9,326,796 | B2* | 5/2016 | Harvey | A61B 17/7032 |
| 9,439,681 | B2* | 9/2016 | Keyer | A61B 17/7037 |
| 9,510,868 | B2* | 12/2016 | Biedermann | A61B 17/7035 |
| 2005/0277927 | A1* | 12/2005 | Guenther | A61B 17/7037 606/308 |
| 2006/0293664 | A1* | 12/2006 | Schumacher | A61B 17/7037 606/254 |
| 2009/0062860 | A1* | 3/2009 | Frasier | A61B 17/701 606/278 |
| 2009/0088809 | A1* | 4/2009 | Fisher | A61M 31/002 606/302 |
| 2010/0204735 | A1 | 8/2010 | Gephart et al. | |
| 2014/0303675 | A1 | 10/2014 | Mishra | |

\* cited by examiner

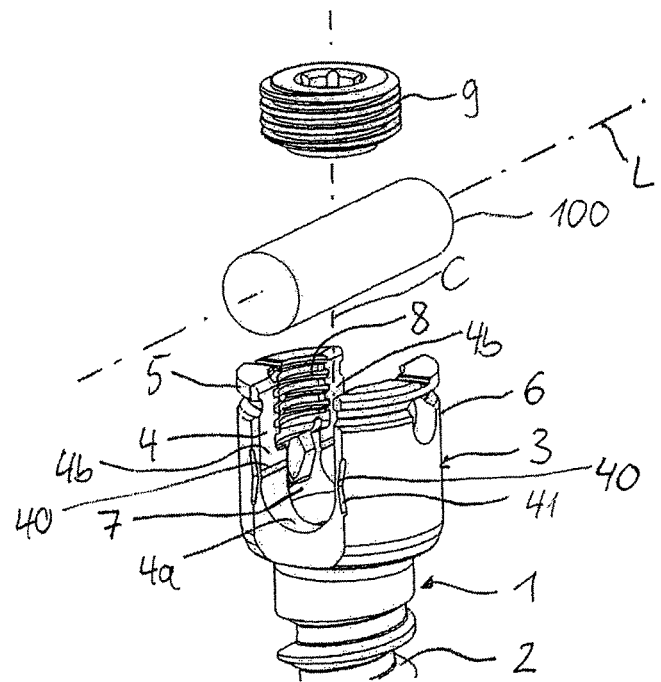
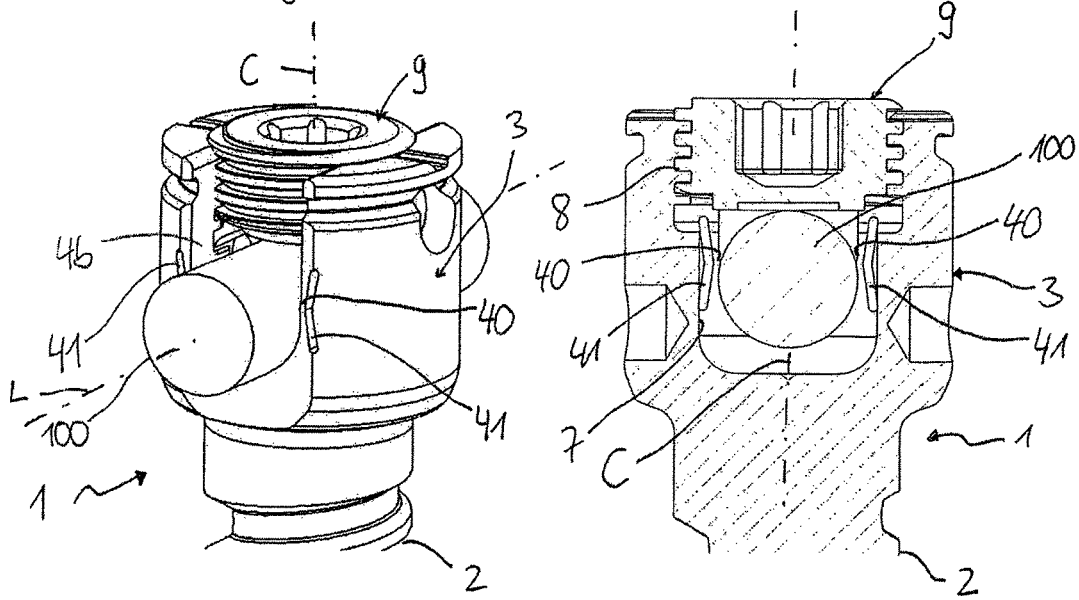
Fig. 1
Fig. 2
Fig. 3

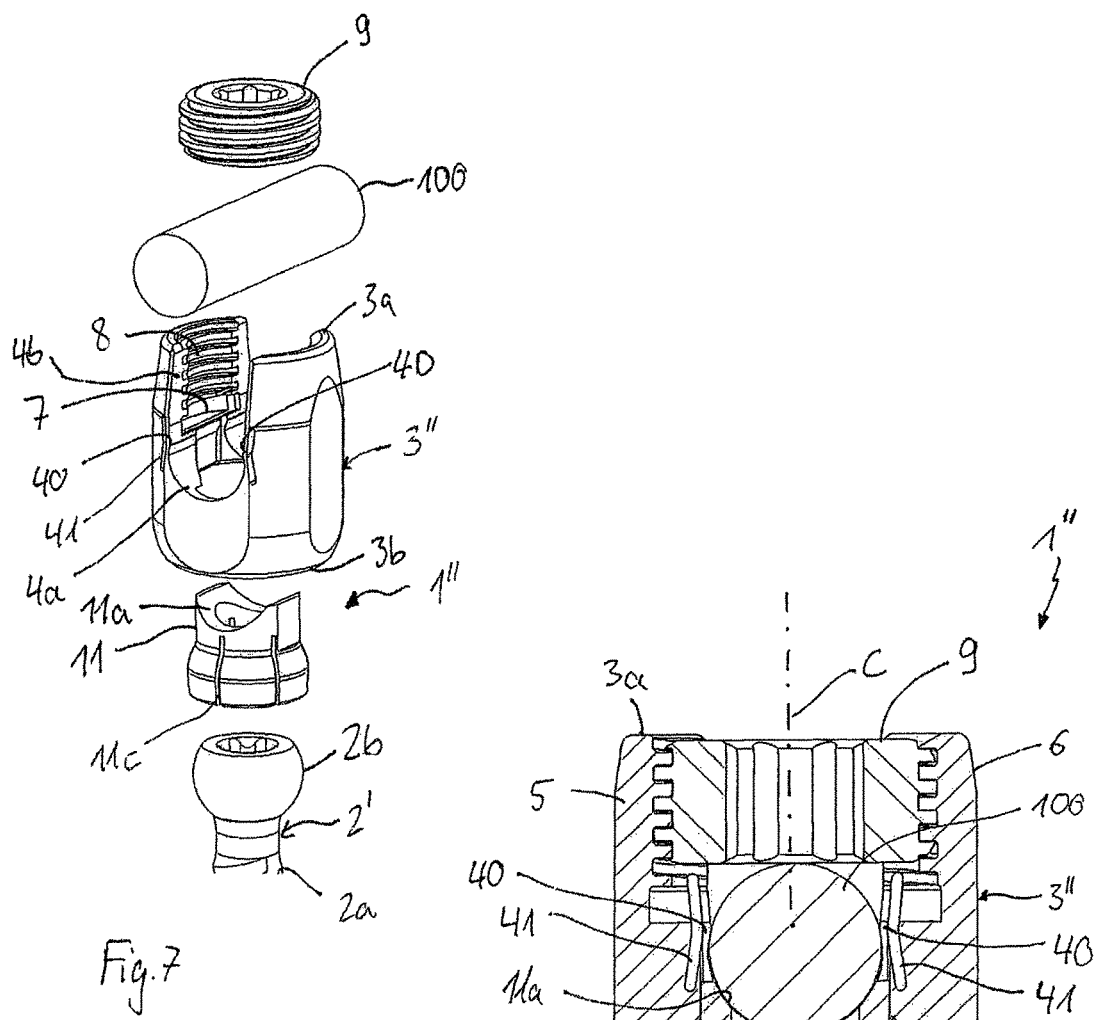

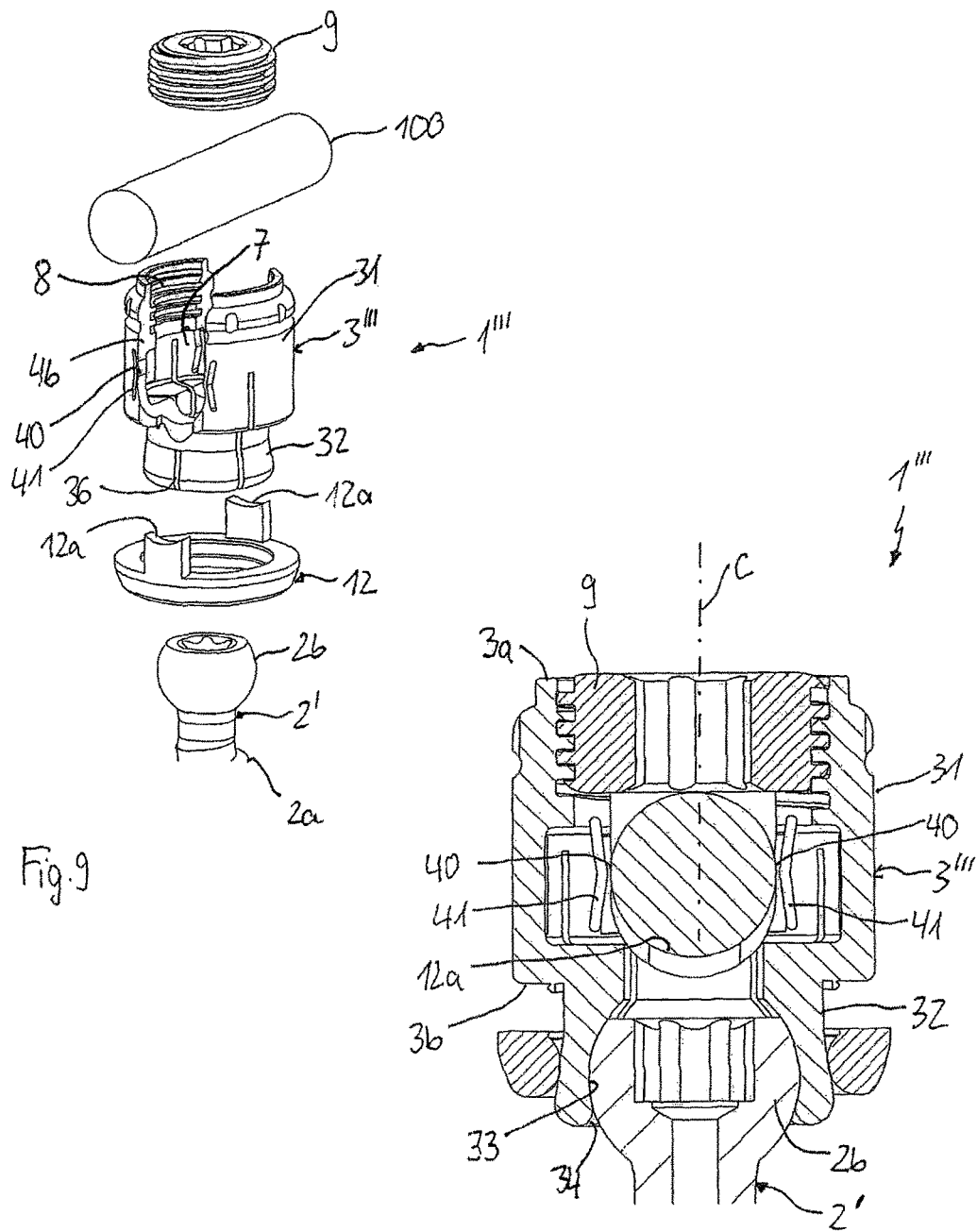

RECEIVING PART FOR COUPLING A BONE ANCHOR TO A ROD AND BONE ANCHORING DEVICE WITH SUCH A RECEIVING PART

CROSS-REFERENCE TO RELATED APPLICATIONS

The present application claims the benefit of U.S. Provisional Application Ser. No. 62/082,517, filed Nov. 20, 2014, the contents of which are hereby incorporated by reference in their entirety, and claims priority to European Patent Application EP 14 194 064.3, filed Nov. 20, 2014, the contents of which are hereby incorporated by reference in their entirety.

BACKGROUND

Field

The present disclosure relates to a receiving part for coupling a bone anchor to a rod and to a bone anchoring device including such a receiving part. More specifically, the present disclosure relates to a receiving part having a recess for receiving a rod therein and at least one resilient retention element for temporarily holding the rod in the recess. The bone anchoring device is particularly suitable for use in spinal stabilization systems.

Description of the Related Art

The process of stabilizing a spinal column using a spinal stabilization system involves the placement of bone anchors, for example pedicle screws, and a rod connecting the bone anchors. During the surgical procedure, the receiving parts of the bone anchors have to be aligned so that the rod can be inserted and finally fixed. It may happen that a rod, once inserted in one of the receiving parts, slips out before it is fixed. This can render the surgical procedure difficult and time consuming, and is therefore not desirable.

From U.S. Pat. No. 7,731,736 B2, a receiver of a bone fixation system is known that automatically provisionally retains a rod when the rod is inserted into the receiver. The receiver includes a rod seat and spaced apart legs that include provisional retention structures in the form of opposing tabs. The tabs project laterally into a pocket of the receiver. Prior to insertion of the rod into the receiver, the legs of the receiver are in a non-deflected orientation. As the rod is pressed downwardly in the pocket, the rod causes the legs to deflect apart to accommodate the rod. In certain embodiments, the partially deflected legs apply a clamping force to the rod.

SUMMARY

Embodiments of the invention provide an improved receiving part for coupling a rod to a bone anchor. Embodiments also provide a bone anchoring device including such a receiving part that allows temporarily holding the rod and that is applicable to various types of receiving parts independent of their specific design.

According to embodiments of the present invention, a receiving part for coupling a bone anchor to a rod is provided that includes a recess for receiving the rod and a bore for inserting a fixation device. A bore axis of the receiving part is substantially perpendicular to a longitudinal axis of the rod to be inserted and the recess has opposing sidewalls and a resilient retention element protruding from at least one of the opposing sidewalls. When the rod is inserted into the recess, the rod can be held temporarily in the recess by the at least one retention element.

Because the retention element is provided on a sidewall of the recess and not within the bore that accommodates the fixation device, any hitherto known design of a receiving part that has a recess for the rod can be provided with such a retention element without substantially changing the design of the receiving part and the design of other parts interacting therewith. The function of the retention element is the same in all types of receiving parts, such as receiving parts of monoaxial bone anchoring devices, receiving parts of polyaxial bone anchoring devices that are of the top-loading type or the bottom-loading type, and receiving parts where the clamping and locking of a head of a bone anchor is achieved by an outer locking ring. After final fixation of the rod with the fixation device, the retention element may have no further function.

The retention element prevents the rod from slipping out of the recess, in particular, from inadvertently slipping-out of the recess during steps of inserting the rod into a plurality of bone anchoring devices or adjustment of the position of a bone anchoring device relative to the rod.

The retention element may be provided at a position in the receiving part such that the retention element exerts a frictional force onto the rod for provisionally holding the rod in a position in the recess.

In a further embodiment, the receiving part with the retention element can be configured such that rods of different diameters can be held. To achieve this, a bottom of the recess that forms a rod seat may have a specific shape, such as a V-groove. Such a configuration allows a single bone anchoring device to be used with rods having different diameters.

In a further embodiment, the retention element may be provided on only one sidewall of the recess. Further, an insertion portion of the recess for inserting the rod may be offset from the bore axis of the receiving part, and the rod seat in the bottom of the channel may be substantially symmetrical to the bore axis. The retention function of the retention element may be enhanced by this configuration.

In a still further embodiment, the retention element is formed by a separate part from the receiving part that is connectable to the sidewall of the recess. Thereby, a material for the retention element can be used that renders the retention element particularly elastic. The material of the retention element may be different from the material of the receiving part.

BRIEF DESCRIPTION OF THE DRAWINGS

Further features and advantages of the present invention will become apparent by the description of embodiments by the means of the accompanying drawings. In the drawings:

FIG. 1 shows an exploded perspective view of one embodiment of a bone anchoring device including a monoaxial bone anchor having a shank (shown only partially) and a receiving part, a rod, and a fixation device;

FIG. 2 shows a perspective view of the bone anchoring device of FIG. 1 in an assembled condition;

FIG. 3 shows a cross-sectional view of the assembled bone anchoring device of FIGS. 1 and 2, the cross-section taken along a plane extending through a bore axis of the receiving part and perpendicular to a longitudinal axis of the rod;

FIG. 7 depicts a further modified embodiment of the bone anchoring device of FIGS. 1 to 3, including a receiving part, a separate bone anchor that is polyaxially connectable to the receiving part, a rod, and a fixation device;

FIG. 8 shows a cross-sectional view of the bone anchoring device of FIG. 7 in an assembled state, the cross-section taken in a plane extending through a bore axis of the receiving part and perpendicular to a longitudinal axis of the rod;

FIG. 9 shows a still further modified embodiment of the bone anchoring device of FIGS. 1 to 3, including a receiving part, a separate bone anchor that is polyaxially connectable to the receiving part and that can be locked by an outer ring, a rod, and a fixation device;

FIG. 10 shows a cross-sectional view of the bone anchoring device shown in FIG. 9 in an assembled state, the cross-section taken in a plane extending through a bore axis of the receiving part and perpendicular to a longitudinal axis of the rod;

FIG. 22b shows a detail of FIG. 22a;

FIG. 24b shows a detail of FIG. 24a;

DETAILED DESCRIPTION

Figure 4A:
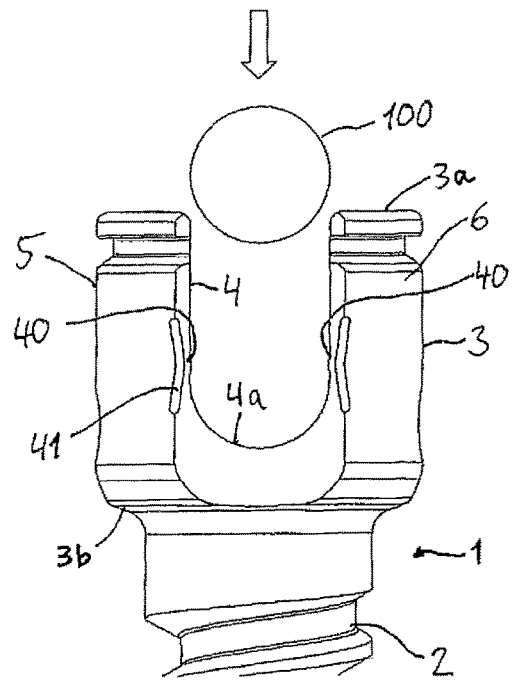
FIGS. 4a to 4d show front views of steps of inserting and holding a rod in the receiving part of the bone anchoring device of FIGS. 1 to 3.

An embodiment of a receiving part is depicted in FIGS. 1 to 3, illustrating a monoaxial bone anchoring device 1. The bone anchoring device 1 has a shank 2 with a bone thread section, a tip (not shown), and a receiving part 3 rigidly connected to the shank 2 for receiving a rod 100 connecting the bone anchoring device 1 to another bone anchoring device 1. The term monoaxial means that the shank axis extends at a fixed angle with respect to the receiving part 3. In the embodiment shown in FIGS. 1 to 3, the angle between the shank axis and the receiving part 3 is zero degrees, but it may be another angle. The receiving part 3 includes a first end 3a and an opposite second end 3b, where the second end 3b is adjacent to the shank 2. At the first end 3a, a channel for the rod 100 in the form of a recess 4 is provided that has a substantially U-shaped cross-section with a bottom 4a of the recess 4 forming a seat for the rod 100. The recess 4 forms two free legs 5, 6. A bore 7 in the receiving part 3 extends from the first end 3a toward the second end 3b and to a depth below the bottom 4a of the recess 4. Adjacent to the first end 3a, an internal thread 8 is provided on the legs 5, 6. The internal thread 8 cooperates with a corresponding external thread of a fixation element or device 9. In the embodiment shown, the fixation element 9 is a set screw. The bore 7 has a bore axis C that is coaxial with the axis of rotation of the threaded shank 2. Opposing sidewalls 4b of the recess 4 are formed on either side of the bore 7, hence, one pair of opposing sidewalls 4b is respectively arranged on each side of the bore 7.

On each of the sidewalls 4b of the recess 4, a retention element 40 is provided that is configured to reduce a width of the substantially U-shaped recess 4 in a direction perpendicular to the bore axis C. The retention elements 40 protrude into the recess 4 such that a distance between two respectively opposing retention elements 40 is smaller than a width of the rod 100. In the case of the cylindrical rod 100 according to the embodiment in FIGS. 1 to 3, the distance between the retention elements 40 of respectively opposing sidewalls 4b is smaller than a diameter of the rod 100. The retention elements 40 have the shape of ribs that extend perpendicular to the bore axis C and parallel to a longitudinal axis L of the rod 100. The retention elements 40 are positioned in an axial direction of the bore axis C at or above a center of the rod 100 measured from the bottom 4a of the recess 4 when the rod 100 is inserted and supported therein.

The retention elements 40 are resilient. In particular, the retention elements 40 of this embodiment are formed as a monolithic piece with each respective sidewall 4b. The resiliency of the retention elements 40 is such that when the rod 100 is inserted into the recess 4, the retention elements 40 are configured to move outward, i.e., away from the bore axis C, such that the distance between the retention elements 40 increases so that the rod 100 can pass therethrough. When the rod 100 is removed from the recess 4 and pressure is no longer exerted onto the retention elements 40 by the rod 100, the retention elements 40 return to their original shape, thereby again restricting the width of the recess 4.

The resiliency of the retention elements 40 is achieved by an angled slit or recess 41 in each of the respective sidewalls 4b. Each recess 41 completely extends through the respective sidewall 4b from an outside of the receiving part 3 and extends into the bore 7 in a direction substantially perpendicular to the bore axis. Hence, the recesses 41 are open at two sides. A cross-section of the recesses 41 resembles a V-shape with an obtuse angle between the legs of the V. Due to the recess 41, the ribs that form the retention elements 40 can be pressed outward to move into the space of the recesses 41.

The size, the shape and the position of the recesses 41 can be selected to obtain a desired flexibility of the retention elements 40.

An outer shape of the receiving part 3 may be substantially cylindrical, but any other shape may be contemplated.

The parts of the bone anchoring device 1 are made of a body-compatible material, for example, a body-compatible metal, a body-compatible metal alloy, or a body-compatible plastic material. Examples of such materials are stainless steel, titanium, nickel titanium alloys NiTi, for example Nitinol, β-titanium and PEEK (polyether ether ketone). In particular, the portion of the bone anchoring device 1 including the retention elements 40 may be made from a material that provides highly elastic properties, such as, for example, super-elastic shape memory alloys such as Nitinol or β-titanium. Additionally, the bone anchoring device 1 or parts thereof can be at least partially made of biodegradable materials. In particular, such materials include degradable polymers, such as, for example, PLLA (poly-L lactide), degradable metals, such as, for example, magnesium, or degradable metal alloys, for example magnesium-based or iron-based alloys.

Figure 4B:
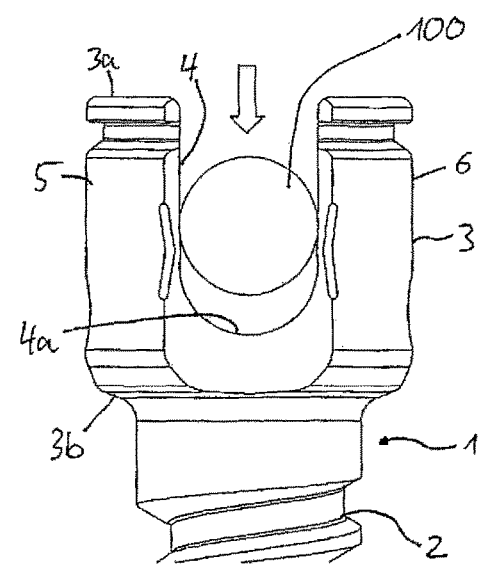
Figure 4C:
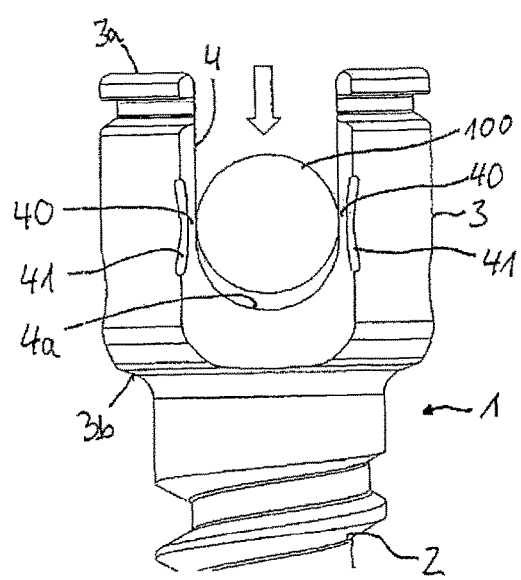
Figure 4D:
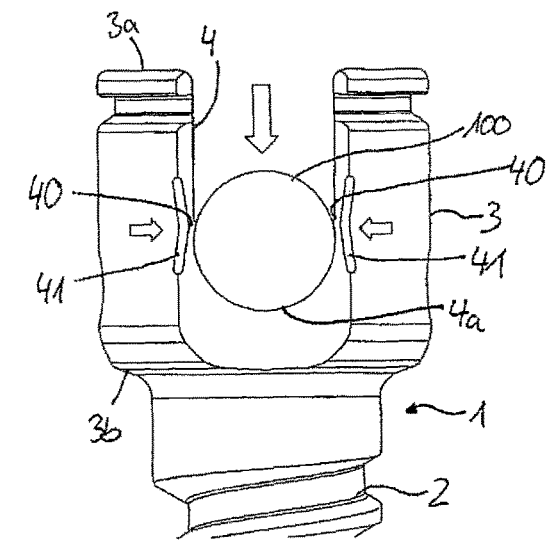

In use, once the shank 2 of the bone anchoring device 1 is anchored to a bone or vertebra, the rod 100 can be inserted into the receiving part 3 and can be held therein as depicted in FIGS. 4a to 4d. As can be seen in FIG. 4a, in their resting position, the retention elements 40 narrow the channel for the rod 100 such that the distance between the innermost surfaces of respectively opposing retention elements 40 is smaller than a diameter of the rod 100. Next, as shown in FIG. 4b, when the rod 100 is inserted into the receiving part 3, the rod 100 cannot automatically pass between the retention elements 40. If the rod 100 is pressed downward, the rod 100 exerts a transverse force onto the retention elements 40, as depicted in FIG. 4c. The retention elements 40 are deflected outward and the channel is widened to let the rod 100 pass therethrough. Finally, when the rod 100 is seated on the bottom 4a of the recess 4, the retention elements 40 tend to return to their original shape due to their resiliency, thereby exerting a transverse frictional force onto the rod 100 that holds the rod 100 provisionally, for example, until final fixation by the fixation device 9. The rod 100 may be held both in the vertical position (i.e., in the rod seat at the bottom 4a of the recess 4), and also in the horizontal position (i.e., the rod's 100 position along the length of the channel).

In a non-deflected condition, the position of the ribs is such that the retention elements 40 are at or above an area with the greatest diameter of the rod 100 when the rod 100 is seated in the bottom 4a of the recess 4, i.e., at an axial position at or above the radius of the rod 100 as measured from the bottom 4a of the recess 4. As such, the rod 100 is prevented from moving out through the first end 3a of the receiving part 3 once the rod 100 is seated.

Figure 5:
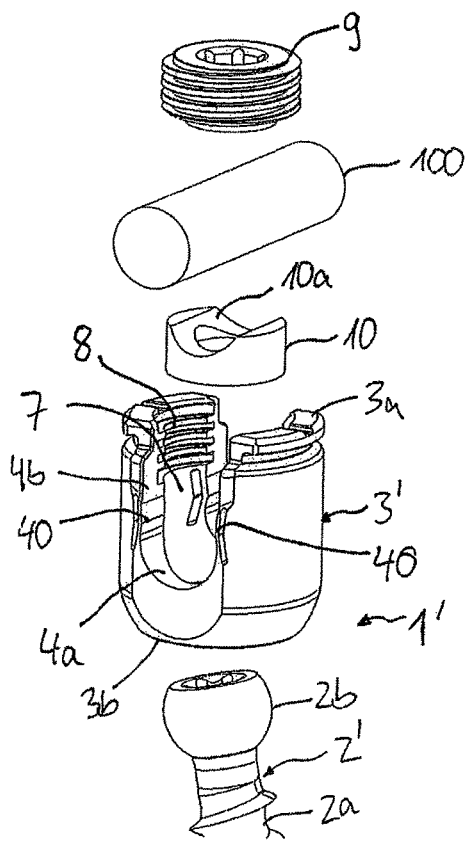
FIG. 5 shows an exploded perspective view of a modified embodiment of the bone anchoring device of FIGS. 1 to 3, including a receiving part, a separate bone anchor that is polyaxially connectable to the receiving part, a rod, and a fixation device.
Figure 6:
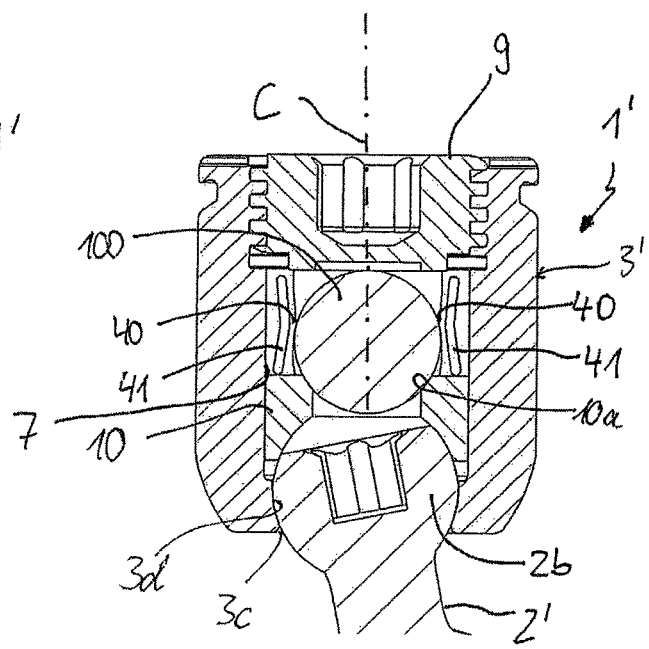
FIG. 6 shows a cross-sectional view of the modified embodiment of the bone anchoring device according to FIG. 5 in an assembled state, the cross-section taken along a plane extending through a bore axis of the receiving part and perpendicular to a longitudinal axis of the rod.

A modified embodiment of a receiving part 3' is explained with reference to FIGS. 5 and 6, depicting a polyaxial bone anchoring device 1'. Parts and portions that are identical or similar to the parts and portions of the previous embodiment are described with the same reference numerals and the detailed description thereof is not repeated. An example polyaxial bone anchoring device 1' includes a bone anchor 2' that has a shank 2a and a head 2b, which may be a spherical segment-shaped head. A receiving part 3' includes, in addition to the portions of the previous embodiment, an opening 3c at the second end 3b and a seat 3d for the head 2b of the bone anchor 2'. The seat 3d can be a spherically-shaped seat or any other seat that allows the head 2b of the bone anchor 2' to pivot therein. The seat 3d is in communication with the bore 7. The example polyaxial bone anchoring device 1' is of the top-loading type, i.e., the bone anchor 2' is inserted into the receiving part 3' from the top or first end 3a. A pressure element 10 is provided that is arranged in the bore 7 and that is configured to exert pressure onto the head 2b of the bone anchor 2' to lock the head 2b in a desired angular orientation with respect to the receiving part 3'. Hence, the term polyaxial means that the shank 2a of the bone anchor 2' can assume various angles with respect to the receiving part 3'. Furthermore, the pressure element 10 provides a support surface 10a for the rod 100, which forms the rod seat in this embodiment. The retention elements 40 are identical or similar to the retention elements 40 of the previous embodiment. In an assembled state as shown in FIG. 6, when the head 2b of the bone anchor 2' is in the seat 3d, when the pressure element 10 is on top of the head 2b, and when the rod 100 is inserted, the position of the retention elements 40 is such that the ribs are at an axial distance from the rod support surface 10a of the pressure element 10 that is equal to or greater than the radius of the rod 100.

A further modified embodiment will be explained with reference to FIGS. 7 and 8. Parts and portions that are identical or similar to parts and portions of the previous embodiments will be described with the same reference numerals and the description thereof is not repeated. The bone anchoring device 1" shown in FIGS. 7 and 8 is an example polyaxial bone anchoring device of the bottom-loading type. The bone anchoring device 1" includes a separate bone anchor 2' as in the previous embodiment and a receiving part 3". The receiving part 3" includes an opening 3c" at the second end 3b that is larger than the diameter of the head 2b of the bone anchor 2'. Furthermore, the receiving part 3" has an accommodation space 3e" that narrows in a narrowing portion 3d" towards the lower opening 3c". The accommodation space 3e" accommodates the head 2b and a cap-like pressure element 11 including a cap-like portion 11b that is flexible due to slits 11c and extends over the area with the greatest outer diameter of the spherical segment-shaped head 2b. Opposite to the cap-like portion 11b, the pressure element 11 includes a rod support surface 11a for supporting the rod 100, which forms a rod seat in this embodiment. The dimensions of the receiving part 3" and the pressure element 11 are such that when the pressure element 11 is placed in the receiving part 3", the pressure element 11 can assume an inserting position in which the cap-like portion 11b can expand in the accommodation space 3e" to allow insertion of the head 2b. Next, the pressure element 11 can assume a pre-locking position in which the pressure element 11 is moved downward when the head 2b is inserted therein such that the cap-like portion 11b is clamped in the narrowing portion 3d'' of the accommodation space 3e'' to prevent removal of the inserted head 2b. Finally, the pressure element 11 can assume a locking position, in which the pressure element 11 and the inserted head 2b are moved downward to such an extent that the head 2b is locked by a clamping force exerted by the narrowing portion 3d'' onto the cap-like portion 11b and the head 2b. As in the previous embodiments, the retention elements 40 are provided in the sidewalls 4b of the recess 4 of the receiving part 3''. The retention elements 40 are located at such a height that an inserted rod 100 that is placed onto the rod support surface 11a is held in this position by the retention elements 40.

A still further modified embodiment will be explained with reference to FIGS. 9 and 10. The bone anchoring device 1''' shown in FIGS. 9 and 10 is a bottom-loading polyaxial bone anchoring device, where the head 2b of the bone anchor 2' is clamped by an outer ring. The receiving part 3''' has a rod-receiving portion 31 that includes the recess 4 forming the channel for the rod 100, the retention elements 40, and the bore 7. Adjacent to the rod-receiving portion 31, a head-receiving portion 32 is provided that has a hollow interior 33 with an opening towards the second end 3b and a flexible wall that is flexible due to slits 36 that are open to the second end 3b. The hollow interior 33 is sized and shaped to accommodate the head 2b therein. The head 2b may be held in the head-receiving portion 32 by friction. A locking ring 12 is provided that extends around the head-receiving portion 32. Two opposite projections 12a on the locking ring 12 may form the rod seat in this embodiment. The locking ring 12 can be moved from a first position closer to the rod-receiving portion 31, which allows insertion of the head 2b through the lower opening 34 until the head-receiving portion 32 covers the head 2b through pressure with the rod 100. The locking ring 12 can be moved to at least a second position in which the locking ring 12 is closer to the second end 3b than in the first position and in which the head 2b is prevented from moving out through the lower opening 34. The locking ring 12 may further assume a third position even closer to the second end 3b than the second position in which the locking ring 12 compresses the head-receiving portion 32 such that the head 2b is locked.

Figure 11:
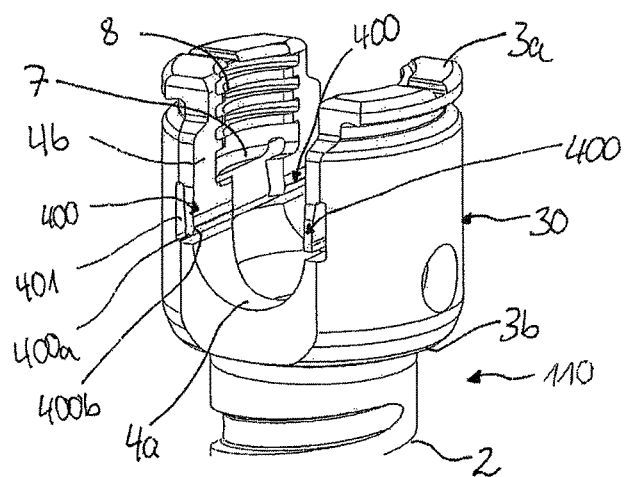
FIG. 11 shows a perspective view of a still further embodiment of a bone anchoring device in the form of a monoaxial bone anchoring device including a receiving part and a shank (shown only partially) connected thereto.
Figures 12A, 12B:
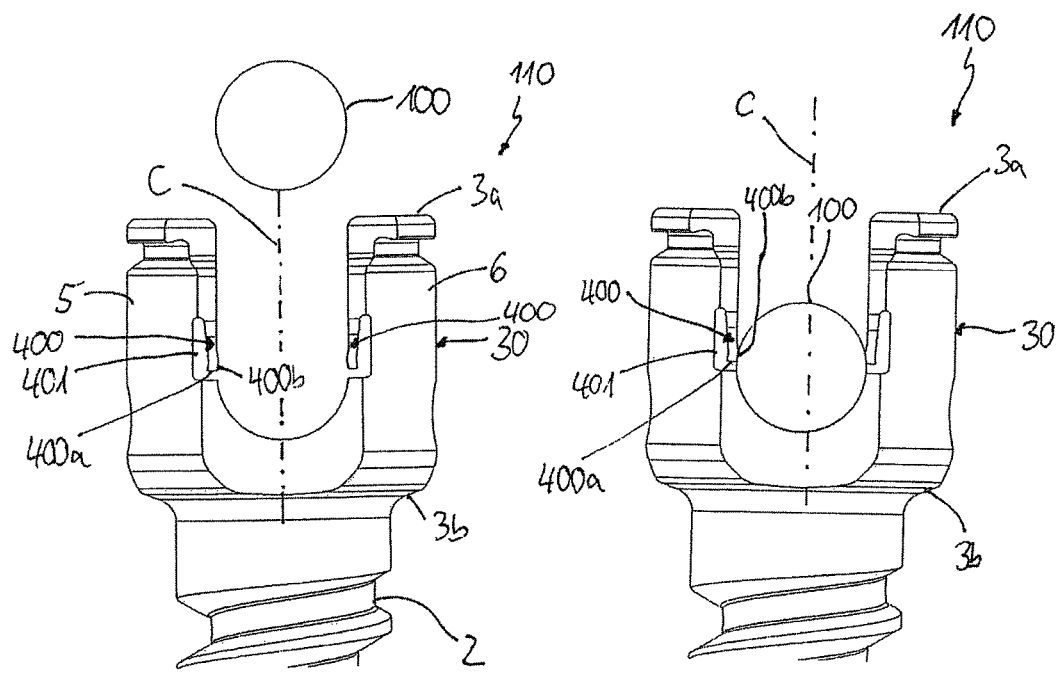
FIGS. 12a and 12b show front views of steps of inserting a rod into the bone anchoring device according to FIG. 11.
Figures 13, 14:
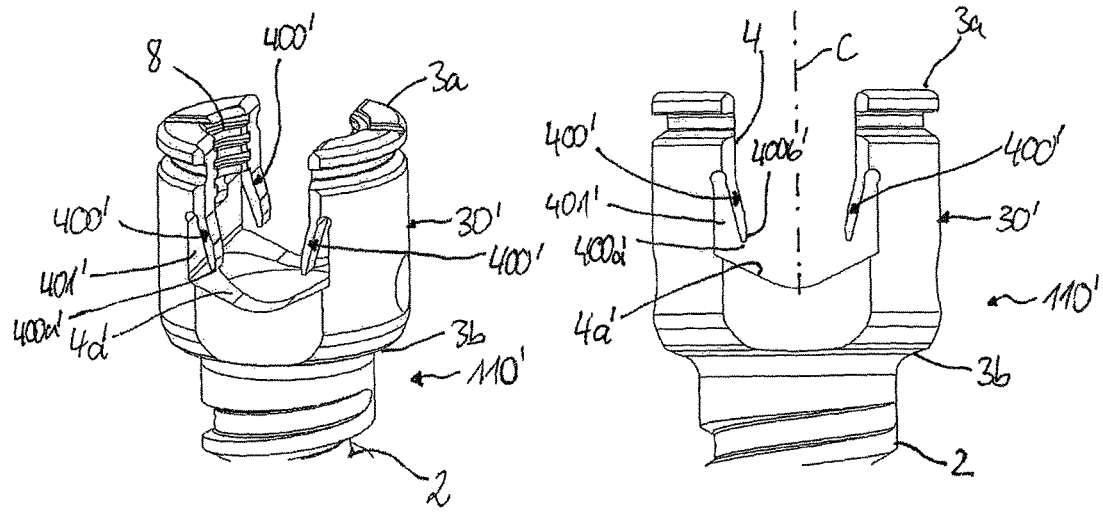
FIG. 13 shows a perspective view of a still further embodiment of a bone anchoring device in the form of a monoaxial bone anchoring device including a receiving part and a shank (shown only partially) connected thereto.
FIG. 14 shows a front view of the bone anchoring device of FIG. 13.

A further embodiment is shown in FIGS. 11, 12a and 12b. The bone anchoring device in this embodiment is shown as a monoaxial bone anchoring device 110 with a shank 2 rigidly connected to a receiving part 30. The receiving part 30 is similar to the receiving part 3 of FIGS. 1 to 3. Identical or similar parts and portions are indicated with the same reference numerals and the description thereof will not be repeated. The receiving part 30 differs from the previous embodiments in the design of the retention elements. The retention elements 400 each are shaped as resilient flaps having a free end 400a and are monolithically connected to the sidewall 4b at the end of the retention elements 400 opposite to the free end 400a. A recess or slit 401 provides space for deflection of the retention elements 400. The orientation of the flaps is such that the free end 400a is directed toward the second end 3b of the receiving part 30. As can be seen in FIG. 11, each recess 401 is open toward three sides. Adjacent to the free end 400a, an inner surface portion 400b of the retention elements 400 (i.e., a surface portion pointing toward the inside of the channel for the rod 100) is concavely shaped with a shape matching the shape of the rod 100. The retention elements 400 protrude into the channel such that when the rod 100 is not inserted in the receiving part 30, a shortest distance between respective retention elements 400 is smaller than the diameter of the rod 100 to be inserted.

In use, when the rod 100 is inserted, the rod 100 slides along the inner surface of the retention elements 400 and deflects the retention elements 400 outward and into the recesses 401. When the rod 100 is seated in the bottom 4a of the U-shaped recess 4, the rod 100 is clipped-in between the retention elements 400 and is provisionally and temporarily held there by the friction between the surface of the rod 100 and the concave surface portion 400b of the retention elements 400.

A modified embodiment is shown in FIGS. 13 to 16. The monoaxial bone anchoring device 110' of FIGS. 13 to 16 is configured to be used with at least two rods 100, 1000 having different diameters. The receiving part 30' differs from the receiving part 30 of FIGS. 11 to 12b in the shape of the retention elements and in the shape of the bottom of the recess forming the channel. The recess 4' forming the channel has a bottom 4a' that is not substantially circular. More specifically, the bottom 4a' is substantially V-shaped. The substantially V-shaped bottom 4a' allows placing rods 100, 1000 with different diameters in the channel, in particular cylindrical rods. When a cylindrical rod is used, the rod 100, 1000 has at least two lines of contact in a direction parallel to the longitudinal axis of the rod such that the rod is safely supported by the at least two lines of contact regardless of the diameter of the rod 100, 1000. The retention elements 400' are formed as flaps as in the previous embodiment. The flaps extend inward into the channel such that a cross-section of the recesses 401' is substantially triangular. A closed end portion 401a' of the recesses 401' may be enlarged and may have, for example, a cross-section that is a portion of a circle to facilitate bending of the flaps of the retention elements 400'. The inwardly protruding flaps reduce the width of the channel for the rod such that rods with a smaller diameter can be used and temporarily held. An inner surface of the retention elements 400' that faces toward the inside of the channel may have several concave surfaces portions 400b' at different positions to grip a corresponding rod 100, 1000.

Figures 15, 16:
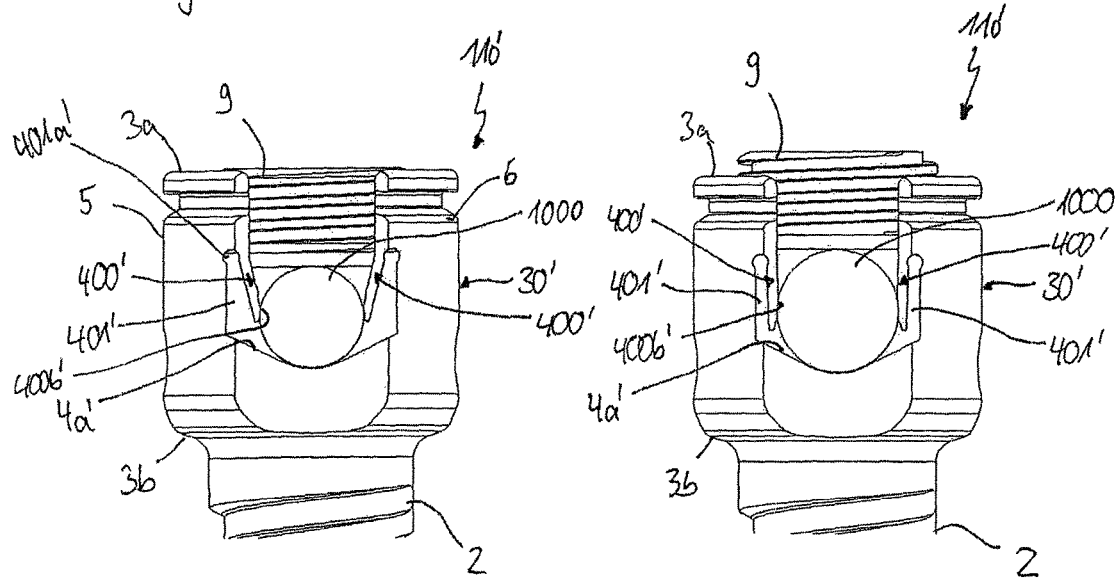
FIG. 15 shows a front view of the bone anchoring device of FIGS. 13 and 14 with a rod having a first diameter inserted therein and a fixation device.
FIG. 16 shows a front view of the bone anchoring device of FIGS. 13 and 14 with a rod having a second diameter inserted therein and a fixation device.
Figure 17:
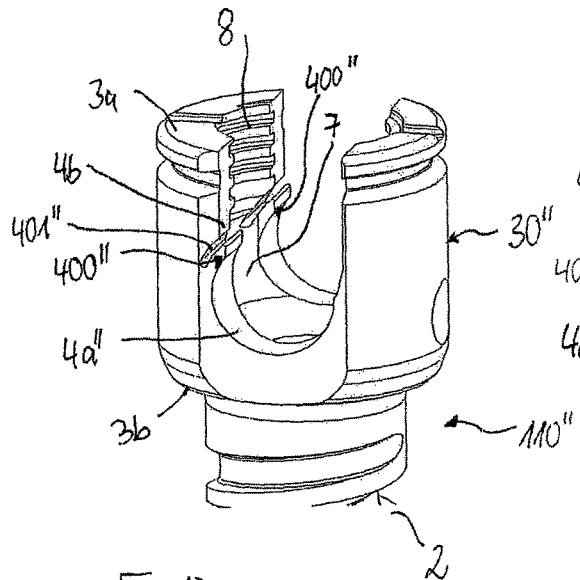
FIG. 17 shows a perspective view of a still further embodiment of a bone anchoring device including a receiving part and a shank (shown only partially) connected thereto.
Figure 18:
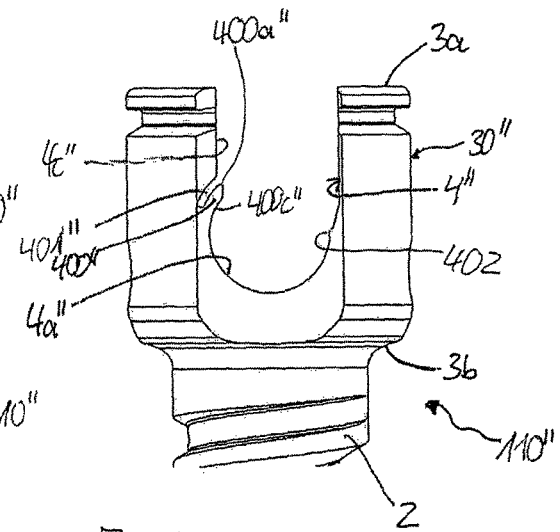
FIG. 18 shows a front view of the bone anchoring device of FIG. 17.

As depicted in FIG. 15, when a first rod 100 with a smaller diameter is used, for example a rod of a diameter of 4.5 mm, the retention elements 400' are only slightly deflected outward into the recesses 401'. As the rod 100 is supported along at least two contact lines in the bottom 4a' of the channel, the rod 100 is safely provisionally held by the retention elements 400' and the bottom 4a' of the channel. As illustrated in FIG. 16, when a rod 1000 with a larger diameter is used, for example a rod with a diameter of 5.5. mm, the rod 1000 deflects the retention elements 400 outward into the recesses 401' to a greater degree as compared to the smaller rod 100. Due to the resiliency of the retention elements 400', the angle of outward deflection when inserting the rod 100, 1000 can vary in a stepless manner. Hence, a variety of rods that differ in diameter can be temporarily held in the receiving part 30'.

A still further embodiment will be explained with reference to FIGS. 17 to 19b. The monoaxial bone anchoring device 110'' includes a shank 2 that is monoaxially connected to a receiving part 30''. The receiving part 30'' differs from the receiving part of the previous embodiments with respect to the arrangement of the recess for insertion of the rod and the retention elements. As in the previous embodiments, the receiving part 30'' includes a bore 7 with a bore axis C that is coaxial with the shank axis. A recess 4'' extends from the first end 3a of the receiving part 30" and ends in a bottom portion 4a" forming a rod seat that is located at a distance away from the second end 3b. The bottom portion 4a" has a substantially circular segment-shaped cross-section with a center of the circle lying in a plane that extends through the bore axis C. Furthermore, the recess 4" has an insertion portion 4c" with a substantially rectangular cross-section. The insertion portion 4c" extends into the bottom portion 4a" whereby a slightly protruding rib 402 is formed on one of each of the pairs of the opposing sidewalls 4b. The center plane of the insertion portion 4c" is offset from the bore axis C, as depicted in particular in FIGS. 19a and 19b. On each of the sidewalls 4b opposite to the protruding rib 402, a resilient retention element 400" is formed that has a free end 400a" facing the first end 3a of the receiving part 30"'. The resilient retention elements 400" have an inner contour 400c" facing the bore axis C that is substantially cylindrical and adapted to the size of the rod 100 to be received therein. Also, cylinderical segment-shaped recesses 401" provide space for outward deflection of the resilient retention element 400". Hence, in this embodiment, for each pair of opposing sidewalls 4b, there is one rigid retention element 402 in the form of a rib on one sidewall 4b and one resilient retention element 400" on an opposite sidewall 4b.

Figure 19A:
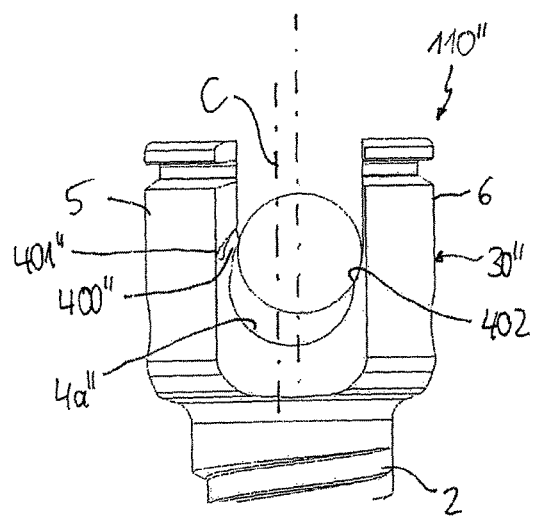
FIGS. 19a and 19b show front views of steps of inserting a rod into the bone anchoring device of FIGS. 17 and 18.
Figure 19B:
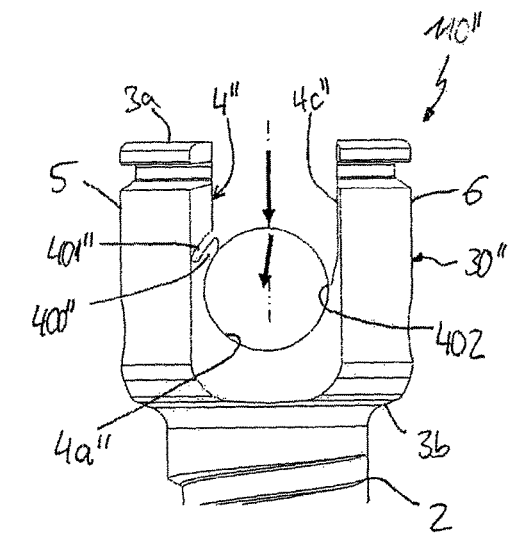
Figure 20:
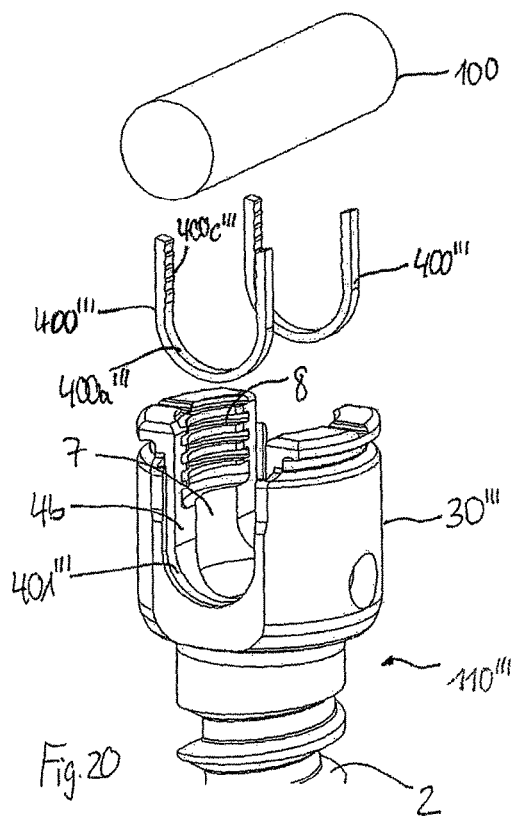
FIG. 20 shows a still further embodiment of a bone anchoring device in the form of a monoaxial bone anchoring device including a receiving part, a shank (shown only partially) connected thereto, separate retention elements, and a rod.
Figure 21:
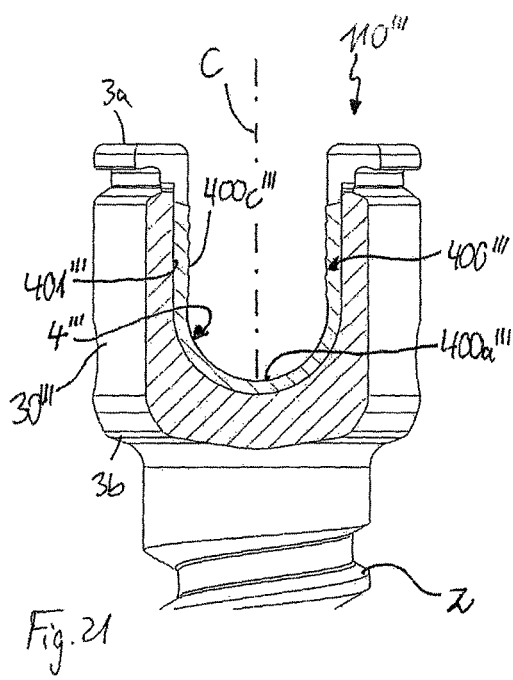
FIG. 21 shows a cross-sectional view of the bone anchoring device of FIG. 20 in an assembled state of the receiving part with the separate retention elements, the cross-section taken in a plane extending parallel to a bore axis of the receiving part and through a sidewall of the channel for the rod.
Figure 22A:
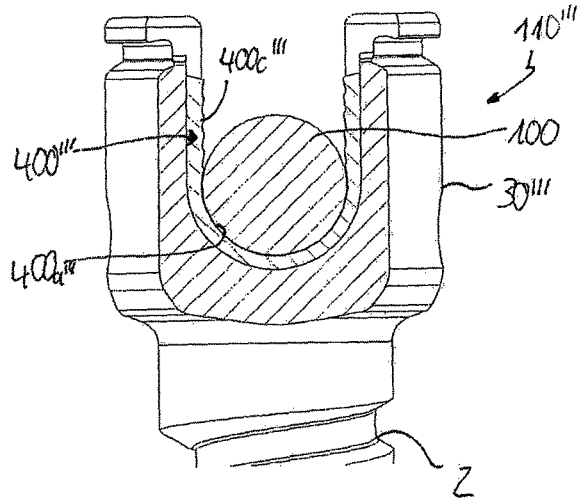
FIG. 22a shows a cross-sectional view of the bone anchoring device of FIG. 20 with the retention elements assembled as in FIG. 21 and with an inserted rod.
Figure 22B:
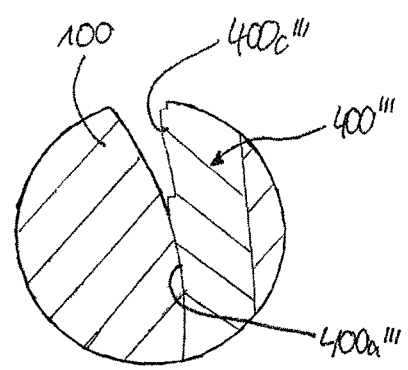

In use, as shown in FIG. 19a, when the rod 100 is inserted through the offset insertion portion 4c", the resilient retention element 400" is deflected outward until the rod 100 passes and snaps into the bottom portion 4a". The rod 100 is then temporarily held in the bottom portion 4a" by the retention elements 400", 402. Because the insertion portion 4c" is offset from a center of the bottom portion 4a", the free end 400a" of the retention elements 400" may be directed toward the insertion portion 4c" when the rod 100 is inserted without obstructing insertion of the rod 100. The gripping of the rod 100 may be enhanced thereby. It shall be noted that the rigid retention element 402 can also be omitted.

A still further embodiment will be explained with reference to FIGS. 20 to 22b. A monoaxial bone anchoring device 110"' according to this embodiment includes a shank 2 rigidly connected to a receiving part 30"'. The receiving part 30"' includes the bore 7 with the bore axis C being coaxial to the shank axis and a substantially U-shaped recess 4"' with a bottom 4a"' for providing a rod seat. In this embodiment, the recess 4"' forming a channel for the rod 100 may be symmetrical to a plane extending through the bore axis C and containing the axis of the rod 100. Each of the sidewalls 4b formed by the substantially U-shaped recess 4"' includes a substantially U-shaped groove 401"' that serves for receiving a separate retention element 400"'. Each separate retention element 400"' is formed as a substantially U-shaped clip with an outer contour shaped to fit into the groove 401"'. The retention elements 400"' also include an inner contour that has a substantially cylinderical segment-shaped bottom portion 400a"' serving as a rod seat and a gripping contour 400c"' between the bottom portion 400a"' and the free ends of the retention element 400"'. The gripping contour 400c"' may have, for example, a teeth-like structure with teeth facing upward toward the first end 3a of the receiving part 30"'. The gripping contour 400c"' serves for slightly clamping the rod 100 in the channel when the rod 100 is inserted therein. In the embodiment shown, the separate retention elements 400"' are provided on either side of the bore 7. The retention elements 400"' may be designed such that when the rod 100 is inserted into the receiving part 30"', the arms of the retention elements 400"' are slightly bent outward toward the groove 401"' and are thereby clamped in the groove 401"'. The material of the retention elements 400"' may be a material that has a greater elasticity than a retention element made of the same material as the receiving part 30"'. For example, the separate retention elements 400"' may be made from a super-elastic body-compatible metal alloy or from a body-compatible plastic material.

In use, when the rod 100 is inserted into the receiving part 30"', the rod 100 presses the arms of the separate retention element 400"' outward so that the retention elements 400"' become clamped in the grooves 401"'. The rod 100 is then held in the bottom portion 400a"' by the gripping contours 400c"' of the retention elements 400"'.

It shall be understood that each of the embodiments described can also be realized in the receiving part of a polyaxial bone anchoring device, as depicted in FIGS. 5 to 10.

Figure 23:
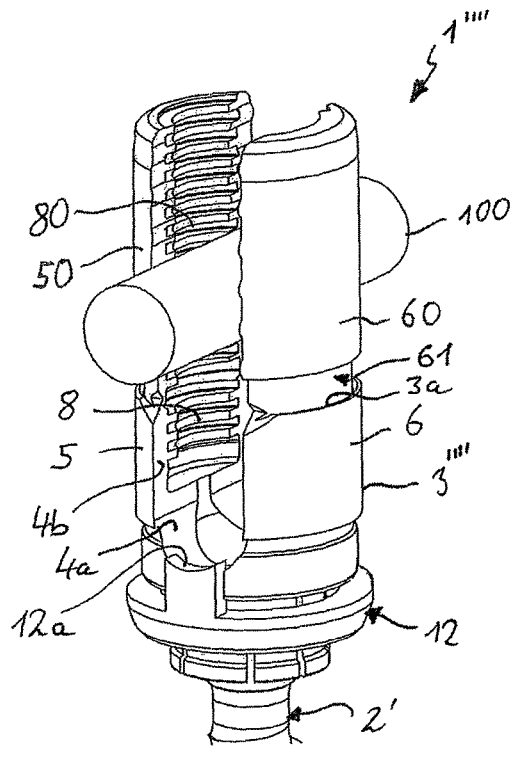
FIG. 23 shows a further embodiment of a bone anchoring device including a receiving part having break-off extension tabs, a bone anchor that is polyaxially connectable to the receiving part and that can be locked by an outer ring, and a rod.
Figure 24A:
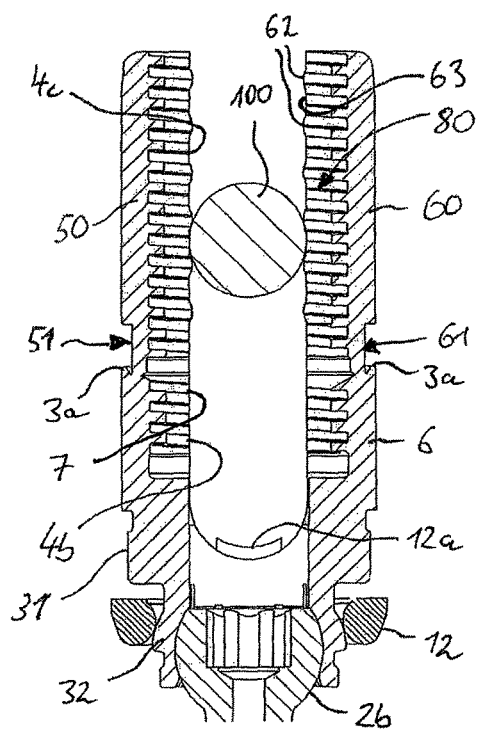
FIG. 24a shows a cross-sectional view of the bone anchoring device of FIG. 23, the cross section taken in a plane extending parallel to a bore axis of the receiving part and through a sidewall of the channel for the rod.
Figure 24B:
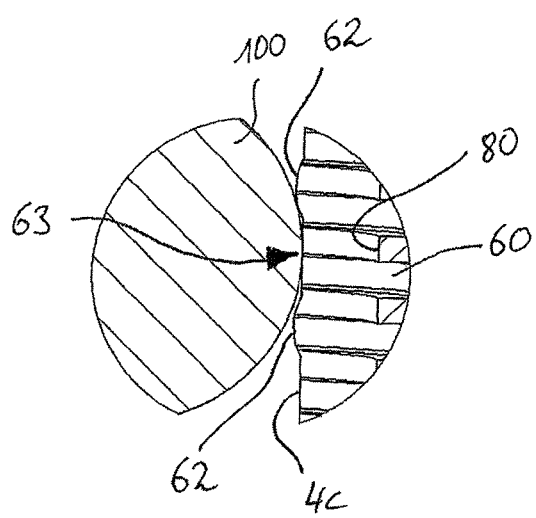

A further embodiment of a bone anchoring device 1"" is shown in FIGS. 23 through 24b. The bone anchoring device 1"" of FIGS. 23 to 24b is similar to the bone anchoring device 1"' shown in FIGS. 9 and 10, and is formed as a bottom-loading polyaxial bone anchoring device, where the head 2b of the bone anchor 2' is clamped by an outer locking ring 12. Only those parts differing from the embodiment of FIGS. 9 and 10 will be explained in the following, while a detailed description of identical or similar features is not repeated herein.

The receiving part 3"" has a rod-receiving portion 31 that includes the recess 4 forming the channel for receiving the rod 100. Moreover, the rod-receiving portion 31 has two legs 5, 6 separated from each other by the recess 4. The two legs 5, 6 include the first end 3a of the receiving part 3"" at respective upper tips of the receiving part 3"". However, before removal thereof, break-off extension tabs 50, 60 monolithically extend from the first end 3a at each of the legs 5, 6, respectively. The use of break-off extension tabs is generally well known in the art. The break-off extension tabs 50, 60 of this embodiment, among other features, help in guiding an inserted rod 100 towards the rod-receiving portion 31 of the receiving part 3"". Once the rod 100 has been guided through the inner sidewalls 4c of the break-off extension tabs 50, 60 and a fixation element 9 (not shown in FIGS. 23 to 24b) has been threaded through an inner thread 80 of the break-off extension tabs 50, 60, the break-off extension tabs 50, 60 may be removed by bending them away around predetermined breaking points 51, 61. The predetermined breaking points 51, 61 are formed as thinned wall portions of the receiving part 3"" at the first end 3a. In this embodiment, the predetermined breaking points 51, 61 are formed as circumferential grooves or cutouts in an outer wall surface of the receiving part 3"".

Due to the predetermined breaking points 51, 61, the break-off extension tabs 50, 60 are resiliently bendable prior to undergoing a bending force sufficient to break-off the extension tabs 50, 60. Further, the opposed inner sidewalls 4c of the break-off extension tabs 50, 60 are separated by a distance that is the same as the distance between the opposed sidewalls 4b of the legs 5, 6 to allow the rod 100 to be guided therethrough to a position in which the rod 100 rests on the projections 12a of the retaining ring 12. However, one or more retention projections 62 may be formed on each of the opposed sidewalls 4c, which narrow the width of the recess 4 between the inner sidewalls 4c in this upper portion. Due to the resiliency of the tabs 50, 60, the rod 100 may, upon insertion, be temporarily held in a flat portion 63 of the sidewalls 4c between two retention projections 62. Also, the tabs 50, 60 bend away from each other when the rod 100 passes opposed retention projections 62 urging the opposed retention projections 62 outwards.

It may be noted that the retention projections 62 may be provided on just one of the two sidewalls 4c. Moreover, the retention projections 62 may form a regular pattern, where, for example, 4 to 6 retention projections 62 are formed on each sidewall 4c, such that a ratchet-like holding mechanism may be established for the rod 100. Such a configuration may give a tactile response to the operator of the bone anchoring device 1"" and further allows the rod 100 to be held at a number of possible vertical positions above the rod-receiving portion 31 according to an operator's specific needs. As the upper ends of the break-off extension tabs 50, 60 move further away from each other at given bending force as compared with portions of the tabs 50, 60 closer to the breakage points 51, 61, the holding force for temporarily holding the rod 100 increases at retention projections 62 positioned closer to the rod-receiving portion 31 (towards the bottom end) allowing the operator to select a temporary holding force for the rod 100 as desired. In this embodiment, the bendable break-off extensions tabs 50, 60, including the retention projections 62, form resilient retention elements.

Further modifications of the embodiments described are possible. The retention elements are not restricted to the specific shapes shown in the embodiments. Deviations therefrom are possible as long as the same function is achieved.

Although the embodiments describe bone anchoring devices where the rod is loaded into the receiving part from a top side of the receiving part, the invention can also be realized in a side-loading device where the rod is insertable into the receiving part from the side, i.e., the insertion direction of the rod includes an angle, for example 90°, with respect to the bore axis.

For the fixation device, all types of known fixation devices can be used, such as dual-part fixation devices, outer nuts, bayonet fixation devices, and others.

For the bone anchor, all types of bone anchors can be used, such as a screw-type bone anchor having a threaded shank, a nail-type bone anchor with or without barbs, a cannulated bone anchor, hooks, and others.

Although the example rods shown in the embodiments are cylindrical rods, the rods do not necessarily need to be cylindrical, but can have another cross-sectional shape such as rectangular, square-shaped, oval-shaped and others. The cross-sectional shape of the rods do not need to be constant over the whole length of the rods. The rods may be smooth or may be roughened or otherwise structured. Also, multi-piece and curved rods may be contemplated.

A number of different embodiments are disclosed herein. It is appreciated that the components of the different embodiments can be mixed and matched to produce other different embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for coupling a bone anchor to a rod, the bone anchor including a shank for anchoring to a bone or a vertebra, the receiving part comprising:
a first end and a second end;
a bore extending from the first end into the receiving part for receiving a fixation device, the bore having a bore axis;
a recess for receiving the rod, the recess being open at the first end of the receiving part and extending toward the second end, wherein a longitudinal axis of the recess intersects the bore axis, such that a first portion of the recess extends through a first side of the receiving part and forms opposing sidewalls that face one another at the first side of the receiving part, and a second portion of the recess extends through an opposite second side of the receiving part; and
a resilient retention element monolithically formed with one sidewall of the opposing sidewalls and spaced apart from the first end of the receiving part,
wherein the resilient retention element is movable from a first configuration wherein the resilient retention element projects into the recess while the opposing sidewalls are separated by a first distance, to a second configuration wherein the resilient retention element is deflected away from the longitudinal axis of the recess toward the one sidewall while the opposing sidewalls remain separated by the first distance.

2. The receiving part of claim 1, wherein the recess forms two opposing legs of the receiving part.

3. The receiving part of claim 1, wherein the resilient retention element protrudes into the recess to such an extent that the resilient retention element is configured to frictionally hold an inserted rod within the recess.

4. The receiving part of claim 1, wherein the resilient retention element is a rib extending perpendicular to the bore axis.

5. The receiving part of claim 1, wherein a second set of opposing sidewalls that face one another is provided at the opposite second side of the receiving part, and wherein at least a second resilient retention element is provided on one sidewall of the second set of opposing sidewalls.

6. A receiving part for coupling a bone anchor to a rod, the bone anchor including a shank for anchoring to a bone or a vertebra, the receiving part comprising:
a first end and a second end;
a bore extending from the first end into the receiving part for receiving a fixation device, the bore having a bore axis;
a recess for receiving the rod, the recess being open at the first end of the receiving, part and extending toward the second end, wherein a longitudinal axis of the recess intersects the bore axis, such that a first portion of the recess extends through a first side of the receiving part and forms opposing sidewalls that face one another at the first side of the receiving part, and a second portion of the recess extends through an opposite second side of the receiving part; and
a resilient retention element provided at one sidewall of the opposing sidewalls, wherein the resilient retention element comprises a plurality of grip elements aligned axially in a direction of the bore axis along the one sidewall to grip the rod, the grip elements configured to project into the recess,
wherein the resilient retention element is deflectable toward the one sidewall.

7. The receiving part of claim 1, wherein the resilient retention element is formed by a protruding portion that protrudes into the recess and that is separated from the one sidewall by a slit.

8. The receiving part of claim 7, wherein the slit is open at two opposite sides.

9. The receiving part of claim 7, wherein the slit is open at three sides.

10. The receiving part of claim 6, wherein the resilient retention element is a separate part from other portions of the receiving part.

11. The receiving part of claim 10, wherein the resilient retention element is a substantially U-shaped clip that is inserted into a groove in the opposing sidewalls.

12. The receiving part of claim 1, wherein a bottom of the recess has a shape that is configured to support at least two rods having different diameters and wherein the resilient retention element is configured to engage rods of different diameters.

13. The receiving part of claim 1, wherein the recess comprises a rod seat portion configured to support an inserted rod and an insertion portion configured to guide the rod toward the rod seat portion, wherein the insertion portion is offset from the rod seat portion in a direction transverse to the bore axis.

14. A bone anchoring device comprising the receiving part according to claim 1, a bone anchor having a shank for anchoring to a bone or a vertebra, and a rod.

15. The receiving part of claim 7, wherein the slit opens to an outside of the receiving part.

16. The bone anchoring device of claim 14, wherein when the rod is located at a bottom of the recess, the resilient retention element is positioned relative to the bottom of the recess at a height in an axial direction of the bore axis that is the same or greater than half a width of the rod.

17. The receiving part of claim 1, further comprising a second resilient retention element monolithically formed with the other sidewall of the opposing sidewalls to form a pair of resilient retention elements.

18. A method of coupling a bone anchor to a rod with a receiving part, the bone anchor including a shank for anchoring to a bone or a vertebra, the receiving part comprising a first end and a second end, a bore extending from the first end into the receiving part for receiving a fixation device, the bore having a bore axis, a recess for receiving the rod, the recess being open at the first end of the receiving part and extending toward the second end, wherein a longitudinal axis of the recess intersects the bore axis, such that a first portion of the recess extends through a first side of the receiving part and forms opposing sidewalls that face one another at the first side of the receiving part, and a second portion of the recess extends through an opposite second side of the receiving part, and a resilient retention element monolithically formed with one sidewall of the opposing sidewalls and spaced apart from the first end of the receiving part, the method comprising:
inserting the rod into the first end of the receiving part;
advancing the rod toward the second end of the receiving part when the resilient retention element is at a first configuration wherein the resilient retention element projects into the recess while the opposing sidewalls are separated by a first distance; and
deflecting the resilient retention element with the rod to a second configuration wherein the resilient retention element is deflected away from the longitudinal axis of the recess toward the one sidewall while the opposing sidewalls remain separated by the first distance.

19. The receiving part of claim 6, wherein the resilient retention element is monolithically formed with the one sidewall.

20. A receiving part for coupling a bone anchor to a rod, the bone anchor including a shank for anchoring to a bone or a vertebra, the receiving part comprising:
a first end and a second end;
a bore extending from the first end into the receiving part for receiving a fixation device, the bore having a bore axis;
a recess for receiving the rod, the recess being open at the first end of the receiving part and extending toward the second end, wherein a longitudinal axis of the recess intersects the bore axis, such that a first portion of the recess extends through a first side of the receiving part and forms opposing sidewalls that face one another at the first side of the receiving part, and a second portion of the recess extends through an opposite second side of the receiving part; and
a resilient retention element provided at one sidewall of the opposing sidewalls and positionable between other portions of the one sidewall and the other sidewall of the opposing sidewalls in a direction perpendicular to the bore axis,
wherein the resilient retention element is movable from a first configuration wherein the resilient retention element projects into the recess while the opposing sidewalls are separated by a first distance, to a second configuration wherein the opposing sidewalls remain separated by the first distance while the resilient retention element is moved to a position outside of the recess, such that a distance between the resilient retention element and the other sidewall of the opposing sidewalls in a direction perpendicular to the bore axis is greater than the first distance.

21. The receiving part of claim 1, wherein the resilient retention element is positionable between other portions of the one sidewall and the other sidewall of the opposing sidewalls in a direction perpendicular to the bore axis.

22. A bone anchoring device comprising the receiving part according to claim 1 and a bone anchor having a shank for anchoring to a bone or a vertebra, wherein the shank is configured to extend from the second end of the receiving part.

* * * * *

UNITED STATES PATENT AND TRADEMARK OFFICE
CERTIFICATE OF CORRECTION

PATENT NO. : 9,861,388 B2  
APPLICATION NO. : 14/946583  
DATED : January 9, 2018  
INVENTOR(S) : Lutz Biedermann et al.

Page 1 of 1

It is certified that error appears in the above-identified patent and that said Letters Patent is hereby corrected as shown below:

In the Claims

Column 12, Line 44, Claim 6      Delete "receiving," and insert -- receiving --

Signed and Sealed this  
Ninth Day of July, 2019

Andrei Iancu  
*Director of the United States Patent and Trademark Office*